US007758507B2

(12) United States Patent  
Yoshikawa et al.

(10) Patent No.: US 7,758,507 B2
(45) Date of Patent: Jul. 20, 2010

(54) BLOOD FLOW IMAGING

(75) Inventors: Hideki Yoshikawa, Kokubunji (JP);
Takashi Azuma, Kawasaki (JP)

(73) Assignee: Hitachi, Ltd., Tokyo (JP)

( * ) Notice: Subject to any disclaimer, the term of this patent is extended or adjusted under 35 U.S.C. 154(b) by 526 days.

(21) Appl. No.: 11/675,711

(22) Filed: Feb. 16, 2007

(65) Prior Publication Data

US 2007/0239014 A1 Oct. 11, 2007

(30) Foreign Application Priority Data

Feb. 22, 2006 (JP) ............................. 2006-044650

(51) Int. Cl.
*A61B 8/00* (2006.01)
*G01S 13/58* (2006.01)
*G01F 1/66* (2006.01)

(52) U.S. Cl. ..................... 600/441; 600/440; 600/453; 600/454; 342/108; 73/861.25

(58) Field of Classification Search .................. None
See application file for complete search history.

(56) References Cited

U.S. PATENT DOCUMENTS

| 5,109,858 | A | * | 5/1992 | Nishiyama et al. | 600/455 |
| 5,513,640 | A | * | 5/1996 | Yamazaki et al. | 600/455 |
| 5,628,321 | A | * | 5/1997 | Scheib et al. | 600/453 |
| 5,910,114 | A | * | 6/1999 | Nock et al. | 600/437 |
| 6,095,980 | A | | 8/2000 | Burns et al. | |
| 6,190,321 | B1 | * | 2/2001 | Pang et al. | 600/441 |
| 6,371,913 | B2 | * | 4/2002 | Pang et al. | 600/441 |
| 6,859,659 | B1 | * | 2/2005 | Jensen | 600/407 |
| 7,044,913 | B2 | * | 5/2006 | Shiki | 600/454 |
| 7,491,173 | B2 | * | 2/2009 | Heim | 600/504 |
| 2002/0013528 | A1 | * | 1/2002 | Pang et al. | 600/441 |
| 2003/0125624 | A1 | * | 7/2003 | Shiki | 600/443 |
| 2005/0154304 | A1 | * | 7/2005 | Robinson | 600/443 |
| 2006/0100518 | A1 | * | 5/2006 | Krishnan | 600/450 |
| 2006/0184032 | A1 | * | 8/2006 | Shiki | 600/454 |

FOREIGN PATENT DOCUMENTS

JP 2001-286472 10/2001

* cited by examiner

*Primary Examiner*—Long V Le
*Assistant Examiner*—Angela M Hoffa
(74) *Attorney, Agent, or Firm*—Antonelli, Terry, Stout & Kraus, LLP.

(57) ABSTRACT

Blood-flow image display equipment for displaying a CFM image that is not affected by a motion of a tissue in an object area during capturing of images or is affected in a reduced manner. The blood-flow image display equipment has the following components: a transmitting controller for controlling transmission triggers of a signal for B-mode and a signal for CFM based on a velocity of motion of an object; an ultrasonic transducer in which piezoelectric ultrasonic transducers each for transmitting/receiving an ultrasonic wave to/from the object are arranged in the form of an array; a B-mode image construction unit for constructing a B-mode image with received signals; a motion detector for measuring a motion vector of the object using the B-mode image; a receiving unit for CFM signal for receiving the signal for CFM from the ultrasonic transducer; a time-series signal storage unit for CFM that collects a CFM measurement region located in the same area of the object based on the motion vector measured by the motion detector and stores them in memory in time sequence; and an autocorrelation processing unit for performing autocorrelation processing on time-series CFM signals.

10 Claims, 14 Drawing Sheets

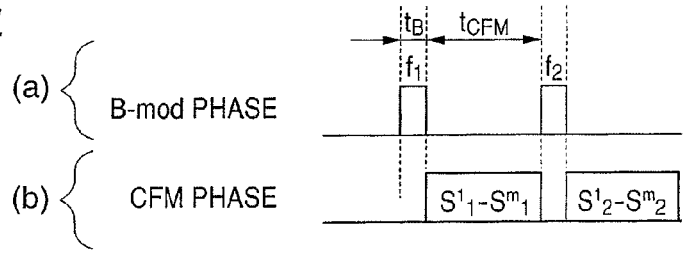
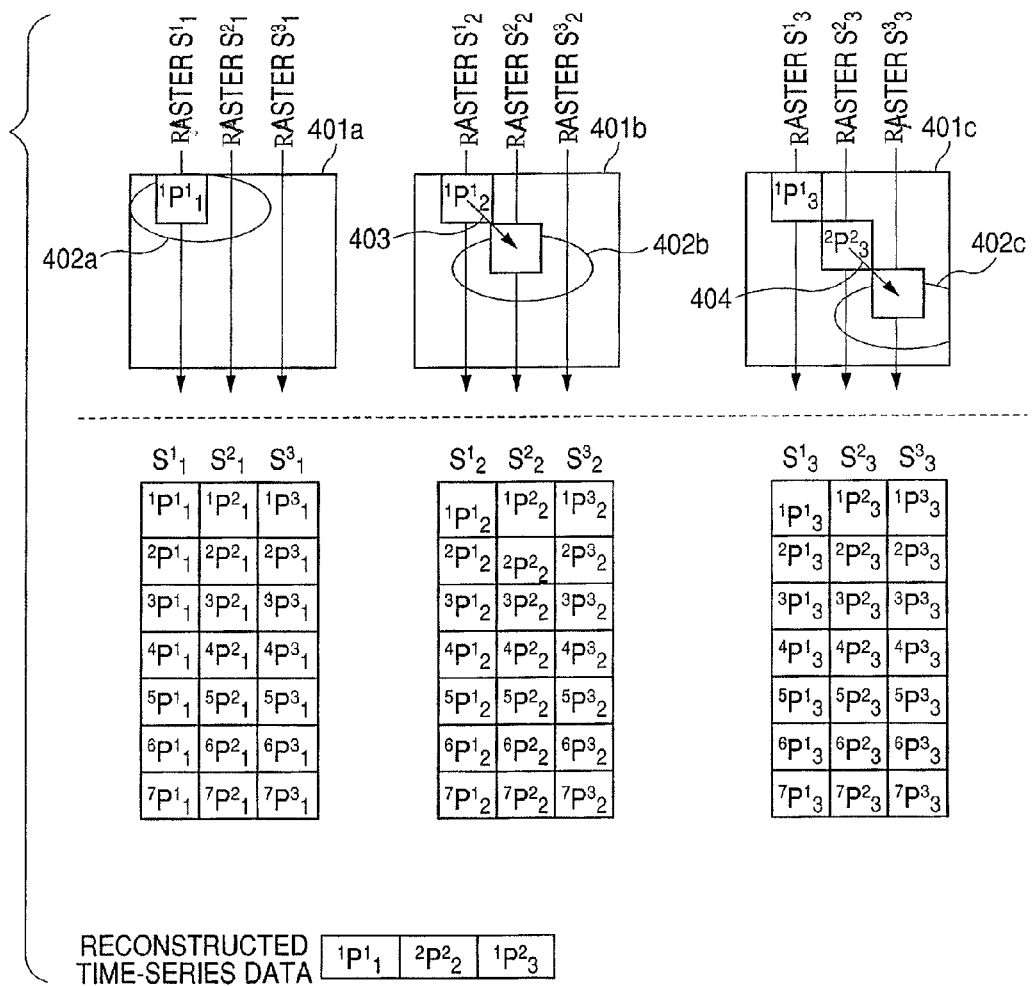

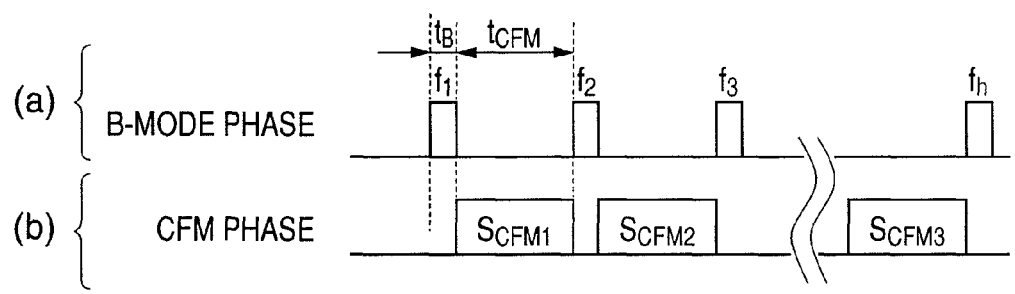
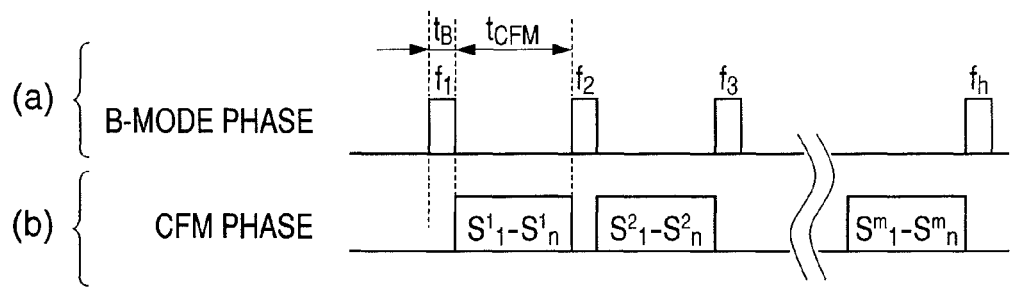

US 7,758,507 B2

BLOOD FLOW IMAGING

CLAIM OF PRIORITY

The present application claims priority from Japanese application JP 2006-044650 filed on Feb. 22, 2006, the content of which is whereby incorporated by reference into this application.

BACKGROUND OF THE INVENTION

The present invention relates to equipment that measures a mean blood flow velocity of an object to be examined using plural ultrasonic signals that are transmitted/received by an ultrasonic transducer, corrects a motion of the object that is being measured using ultrasonic images when constructing a two-dimensional image representing a blood flow distribution, and displays a high-accuracy blood flow image from which an effect of the motion is removed.

FIELD OF THE INVENTION

Since the color flow mapping (CFM) of a blood flow using ultrasonic waves can image a distribution of blood vessels and hemodynamics noninvasively and in real time, it has become an indispensable technology in medical fields as a monitoring tool for diagnosis and treatment.

The blood-flow measurement by ultrasonic wave is performed by doing transmitting/receiving of ultrasonic waves to/from a focused area of the object plural times and measuring a Doppler frequency caused by the blood flow by autocorrelation processing. The measured Doppler frequency enables the mean blood flow velocity and a blood flow direction to be calculated therefrom. A two-dimensional CFM image that is rendered in multiple colors according to a blood flow velocity and the blood flow direction is displayed by performing ultrasonic wave transmitting/receiving two-dimensionally and constructing an image using obtained blood information of areas.

As a method for removing an effect of a motion of tissue and extracting only a signal from a contrast agent flowing in a blood vessel, proposed is a method for correcting a motion of the tissue included in plural received signals from the focused area using an intense reflection echo from the tissue (JP-A No. 286472/2001). Although the technique described in JP-A No. 286472/2001 that aims at extracting a harmonic content included in the reflection echo from the contrast agent is different from the CFM in terms of both object and approach, the problem of removing the motion of the tissue is common. This technology described in JP-A No. 286472/2001 relates to the pulse inversion method (U.S. Pat. No. 6,095,980) for imaging a harmonic content with high sensitivity. Below, the pulse inversion method will be explained briefly. First, two waves whose phases are mutually shifted by 180° are transmitted toward the object and total four reflection echoes including fundamental wave contents and the second harmonic contents of them are received. By performing addition processing of the fundamental wave contents and the second harmonic contests received, respectively, the fundamental contents cancel out each other because their phases are inverted to each other, whereas the second harmonic contents are enhanced twofold because a phase difference of 180° between the sending wave signals is doubled to be 360°. By imaging this second harmonic content, imaging of a blood vessel is possible with high sensitivity. The pulse inversion method is based on the premise that signals from the same area of the object are correctly subjected to addition processing, and if there is a motion of a tissue, there occurs a problem that the fundamental wave contents are not completely erased, yielding a residual, and the second harmonic contents are added while being shifted. The technique described in JP-A No. 286472/2001 uses a fact that a reflection echo from a tissue is extremely intense as compared to that from a blood vessel. The received two reflection echoes are subjected to correction of the motion of the tissue using an intense echo signal from the tissue as a reference by a technique of correlation calculation etc. and subsequently are subjected to addition processing. By this technique, the harmonic content from a blood flow is extracted correctly, and the blood flow can be imaged with high sensitivity.

SUMMARY OF THE INVENTION

In order to measure blood-flow information on the focused area correctly, each of plural received signals used for autocorrelation processing needs to be a reflected signal from the same area of the object. However, since tissues inside an organism are always moving by influences of respiration and heart beat, there is no guarantee that time-series signals obtained by plural times of transmitting/receiving are reflection signals from the same area of the object.

Moreover, when the object is moving, a Doppler frequency to be measures contains both that caused by a blood flow and that caused by a tissue motion. Usually, since a motion of a tissue is slower than that of a blood flow, having a low frequency, only information about the blood flow is extracted by processing with a frequency filter that is typified by the low-cutoff filter. However, since the frequency filtering processing loses information of low-velocity blood flows that are comparable with a motion of a tissue, there remains a problem of decreased measurement accuracy.

In order to obtain a blood flow image in which a motion is corrected by applying a motion correction method described in JP-A No. 286472/2001 to blood flow image imaging, there can be a method for estimating a motion by performing correlation calculation between blood images at different time phases and correcting it, a method whereby a motion is estimated by performing correlation calculation between received RF signals, not the blood flow signals, that serve as a base of calculating blood flow signals and a result is reflected on the blood flow image, and the like. The former is hard to apply to the case where signals are generated only intermittently, such as a case of a blood vessel of an artery, whereas the latter can be applied to even a situation where a blood flow is generated only intermittently, since a RF signal from a tissue always exists. However, in order to obtain a blood flow image in which the motion is corrected using the RF signal in imaging a blood flow image, the method comes with the following problem.

Since a reflection signal from a blood cell is very small as compared to a reflection signal from a biological tissue, sending wave energy is enlarged in imaging a blood flow image. Since from a viewpoint of safety to an organism, the amplitude in ultrasonic tomogram imaging is limited, in order to increase sending wave energy, a sending wave waveform is specified to be long in a temporal axis direction by prioritizing sensitivity other than spatial resolution. This specification deteriorates spatial resolution in the depth direction, resulting in poor accuracy of motion estimation. Moreover, in the blood-flow imaging, in order to prevent the fall of a frame rate caused by performing transmitting/receiving multiple times in order to acquire a signal of one location, the interval of the scanning line is determined coarsely. Therefore, accuracy in the lateral direction is also poor in estimating a motion from the blood flow image signal. Even if the accuracy is sufficient, since the scanning line is coarse, information of positions corresponding to positions after deformation is lost; therefore, even if the conventionally known body motion correction method or a body motion correction method for a range that can be analogized therefrom is performed, a blood flow image imaging of a body-motion-correction integration type is hard to achieve.

The object of this invention is to provide blood-flow image display equipment that corrects deformation of the object and an effect of a motion and displays a blood-flow distribution image in which blood flows, from a low-velocity blood flow to a high-velocity blood flow, are correctly imaged.

In order to attain the object, the blood-flow image display equipment of this invention divides an ultrasonic image into motion measurement areas, measures a motion vector in each motion measurement area, collects only signals from the same area of the object from signals for blood flow measurement (signals for CFM) that are received multiple times based on the motion vector to construct time-series CFM signals, and performs autocorrelation processing on the time-series CFM signals, whereby the blood-flow image display equipment constructs a two-dimensional image that is rendered in multiple colors according to a mean blood flow velocity and a blood flow direction of a focused area, performs this procedure for all the divided measurement areas, and reconstructs the obtained two-dimensional images, and thereby displays a blood-flow distribution image from which an effect of a tissue motion is removed. Especially, for motion estimation, it is important to perform tomograph imaging for motion estimation halfway through CFM imaging in order to attain improved accuracy.

Below, a typical example of construction of the blood-flow image display equipment of this invention will be described.

(1) One example of blood-flow image display equipment has: an input unit of target for inputting information about the object; an ultrasonic transducer for transmitting/receiving ultrasonic waves to/from the object; a transmitting controller for controlling transmission triggers of a signal for B-mode (ultrasonic two-dimensional image) and a signal for CFM (blood flow image); a B-mode image construction unit for constructing a B-mode image from a received signal; a motion detector that divides the B-mode image into the plural motion measurement areas and measures the motion vector of the object in each motion measurement area; a receiving unit for CFM signal for retaining plural received signals for CFM; a time-series CFM signal construction unit that sets a CFM measurement region for the currently-retained signals for CFM, collects the signals for CFM corresponding to the same portion as the CFM measurement region from the plural signals for CFM based on the motion vector measured by the motion detector, and constructs the time-series CFM signals to be used in autocorrelation processing; an autocorrelation arithmetic unit for measuring the mean blood flow velocity and the blood flow direction by autocorrelation processing; and a CFM image display unit that constructs a blood-flow distribution image that is rendered in multi colors according to the velocity of the blood flow and its direction and displays it.

(2) Another example of blood-flow image display equipment is the above-mentioned blood-flow image display equipment (1), wherein a sending wave sequence of the signal for B-mode and the signal for CFM from the ultrasonic transducer is determined by maximums of a motion velocity of an object and of a blood flow velocity to be measured.

(3) Further another example of blood-flow image display equipment is the above-mentioned blood-flow image display equipment (1), wherein the time-series CFM signals to be subjected to autocorrelation processing is constructed with the signals for CFM that are collected based on the motion vector measured by the motion detector.

(4) Still another example of blood-flow image display equipment is one that has: means for determining a sending wave sequence by the motion velocity of the object and the blood flow velocity; means for collecting the signals for CFM corresponding to the same portion as the CFM measurement region from the plural signals for CFM based on a measurement result of the motion vector and constructing the time-series CFM signals; and a CFM image display unit that performs autocorrelation processing on the time-series CFM signals and displays a blood-flow distribution image.

According to the blood-flow image display equipment of this invention, the blood flow measurement that is not affected by the motion of the object is possible, and the high-accuracy blood-flow distribution image containing a low-velocity blood flow that is close to a tissue motion in velocity can be displayed.

BRIEF DESCRIPTION OF THE DRAWINGS

FIGS. 2A and 2B are diagrams explaining a principle of CFM imaging, in which FIG. 2A shows a relation of a receiving echo and time, and FIG. 2B shows phase shift through the receiving echo for several irradiation numbers;

FIGS. 4A and 4B are diagrams showing one example of a sending wave sequence of the signal for B-mode and the signal for CFM in the one type of blood-flow image display equipment of the first embodiment, in which FIG. 4A shows B-mode phase, and FIG. 4B shows CFM phase;

FIG. 5 is a diagram explaining a method for collecting a packet being set for the same area of the object from acquired raster signals based on a body motion measurement result in the blood-flow image display equipment of the one type of first embodiment;

FIGS. 7A and 7B are diagrams showing one example of the sending wave sequence of the signal for B-mode and the signal for CFM in the one type of blood-flow image display equipment of the first embodiment, in which FIG. 7A shows B-mode phase, and FIG. 7B shows CFM phase;

FIGS. 8A and 8B are diagrams showing one example of the sending wave sequence of the signal for B-mode and the signal for CFM in the one type of blood-flow image display equipment of the first embodiment, in which FIG. 8A shows B-mode phase, and FIG. 8B shows CFM phase;

FIGS. 9A and 9B are diagrams showing one example of the sending wave sequence of the signal for B-mode and the signal for CFM in the one type of blood-flow image display equipment of the first embodiment, in which FIG. 9A shows B-mode phase, and FIG. 9B shows CFM phase;

FIGS. 10A and 10B are diagrams showing one example of the sending wave sequence of the signal for B-mode and the signal for CFM in the one type of blood-flow image display equipment of the first embodiment, in which FIG. 10A shows B-mode phase, and FIG. 10B shows CFM phase;

FIGS. 11A and 11B are diagrams showing one example of the sending wave sequence of the signal for B-mode and the signal for CFM in the one type of blood-flow image display equipment of the first embodiment, in which FIG. 11A shows B-mode phase, and FIG. 11B shows CFM phase;

FIGS. 12A and 12B are diagrams showing one example of the sending wave sequence of the signal for B-mode and the signal for CFM in the one type of blood-flow image display equipment of the first embodiment, in which FIG. 12A shows B-mode phase, and FIG. 12B shows CFM phase;

FIGS. 13A and 13B are diagrams showing one example of the sending wave sequence of the signal for B-mode and the signal for CFM in the one type of blood-flow image display equipment of the first embodiment, in which FIG. 4A shows B-mode phase, and FIG. 4B shows CFM phase;

FIGS. 17A and 17B are diagrams illustrating raster positions in the one type of blood-flow image display equipment of a third embodiment, in which FIG. 17A shows three raster positions for first, second, and third transmitting/receiving in the packet, and FIG. 17B shows three raster positions in the case where a signal is detected for several stages divided in the depth direction.

DETAILED DESCRIPTION OF THE PREFERRED EMBODIMENTS

Blood-flow image display equipment of this invention measures a motion vector of an object using a B-mode image, collects signals for CFM that correspond to the same portion as a CFM measurement region from the plural signals for CFM based on the measurement result to construct time-series CFM signals, performs autocorrelation processing on the time-series CFM signals, and displays a blood flow image.

First Embodiment

Figure 2A:
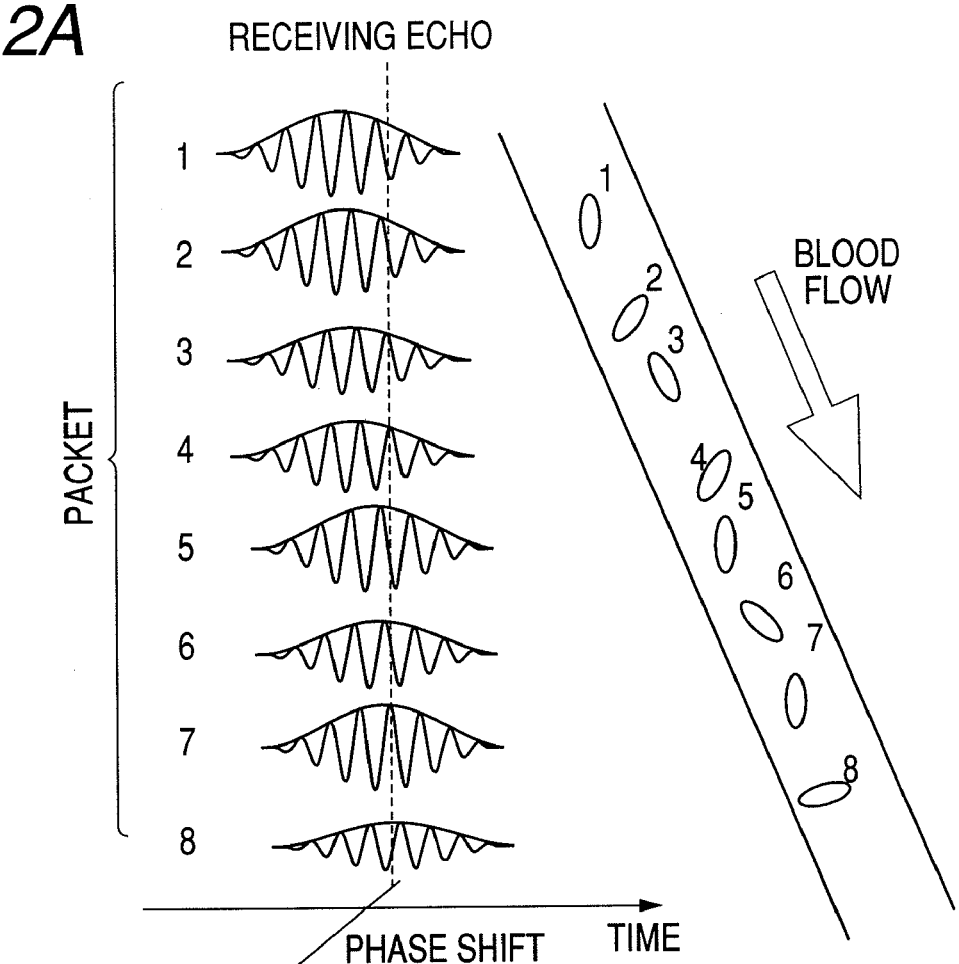
Figure 2B:
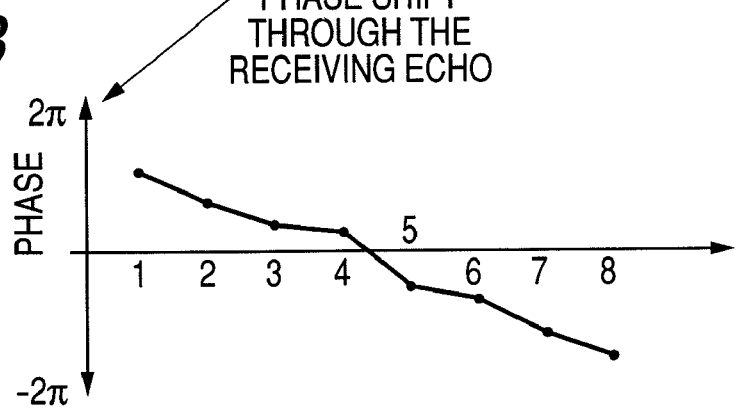

First, an imaging principle of CFM will be explained using FIG. 2. The right-hand side of the figure shows a motion of one blood cell at time 1 to time 8. In order to capture the motion of this blood cell, a signal is transmitted to and received from the same portion multiple times, as one set (in this example eight times), which is called packet wave transmitting/receiving. On the right-hand side of the figure, receiving wave echo signals in each packet when an ultrasonic wave is transmitted/received at time 1 to time 8. Since a distance to the object varies depending on a motion of the object, the receiving wave pulse signals shift on a temporal axis. As shown by a dotted lined in the figure, when viewing the pulse signals at a certain point on the temporal axis, the phase rotates in the packet, as shown by (b) of FIG. 2. From the amounts of phase rotation, a motion velocity of the object at each position is estimated and imaged, which is called CFM imaging. An optimal repetition frequency in the packet depends on the motion velocity of the object. That is, in the case where a fast motion is targeted, a high frequency is needed; in the case where a slow motion is targeted, a low frequency is needed. After acquisition of information for one packet is completed, the flow shifts to the adjacent scanning line (raster) and the same operation is done. By repetition of this operation in all of rasters, information of one screen is acquired and a tomogram is displayed. Since an ultrasonic wave is transmitted to and received from the same portion multiple times, the frame rate is decreased by the number of transmitting/receiving of one packet; therefore, normally, in the CFM imaging, the number of rasters is decreased as compared to the case of B-mode imaging, and an image is formed by interpolation between rasters.

Figure 1:
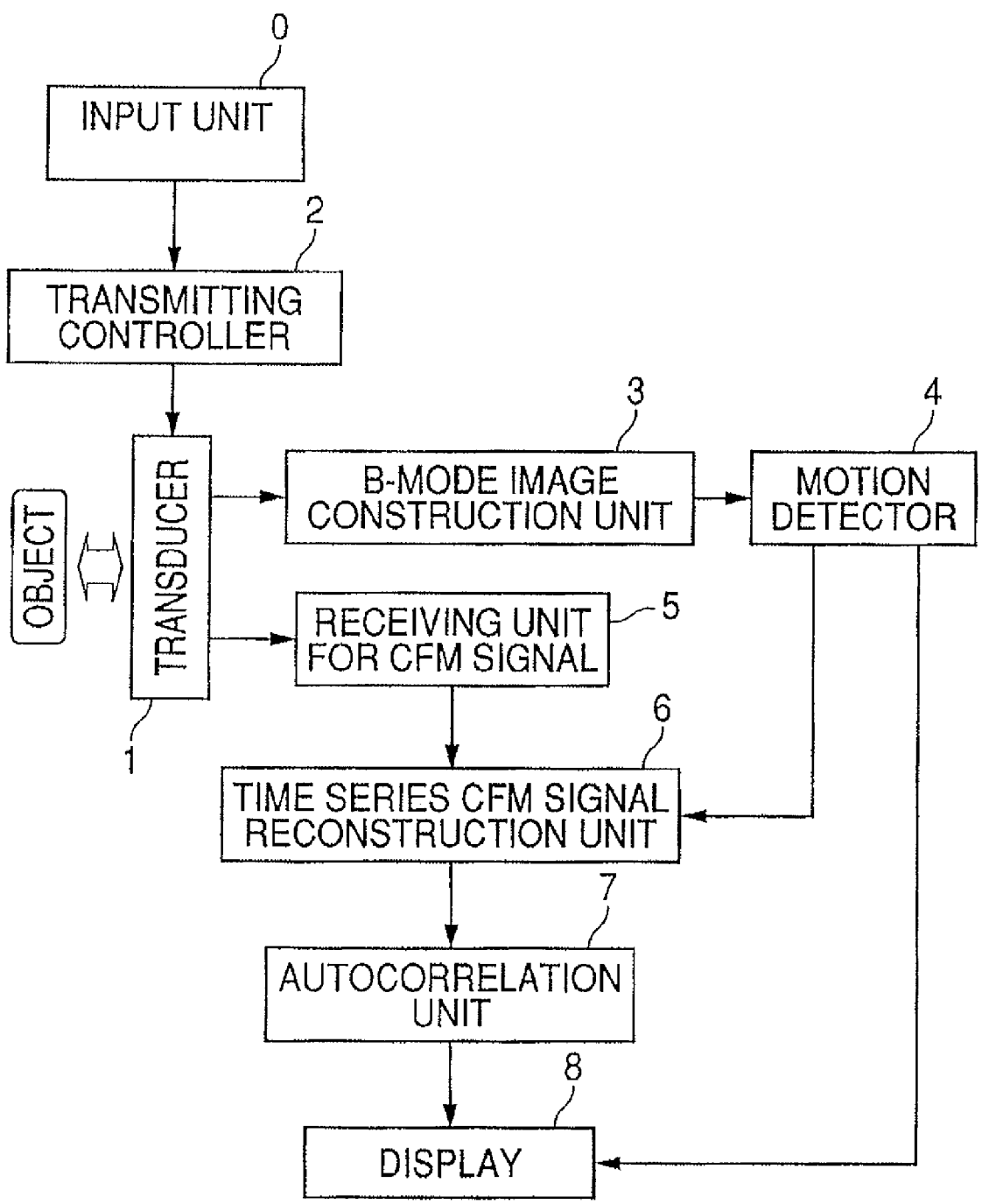
FIG. 1 is a block diagram showing a construction of the one type of blood-flow image display equipment according to a first embodiment.

FIG. 1 is a block diagram showing a construction of a first embodiment of blood-flow image display equipment.

The blood-flow image display equipment of this embodiment performs as follows: It determines a sending wave sequence of a signal for B-mode and a signal for CFM according to the motion velocity of the object and a blood flow velocity, transmits/receives the signal for CFM and the signal for B-mode, following the sending wave sequence, measures the motion vector of the object using the B-mode images acquired before and after the signal for CFM for each motion measurement area that is set on the B-mode image, collects the signals for CFM corresponding to the same area as the CFM measurement region that is set on the signal for CFM received for the first time from the plural signals for CFM based on the measurement result of the motion vector to construct the time-series CFM signals, measures a mean blood flow velocity and a direction of a blood flow by autocorrelation processing using the time-series CFM signals, and displays a CFM image that is rendered in multiple colors according to the velocity of a blood flow and its direction at any time.

First, a construction of the equipment that is responsible for from transmitting/receiving of ultrasonic signals to/from the object to the CFM image display that removes the motion of the object will be explained using the block diagram of FIG. 1.

When the operator collects an object to be examined in an input unit of target 0, a velocity range of measurement that is set beforehand and corresponds to the object is collected. An upper limit of the velocity range is a blood flow velocity that is an upper limit up to which the measurement is done. It is also necessary to set a lower limit as well as the upper limit. This is because, since the reflection echo intensity from a biological tissue having a motion is larger than the echo intensity from a blood flow, if low-velocity components below a certain threshold are not cut off, the blood flow signal is masked with a signal from the organism and becomes disappeared. The inputted velocity range is sent to a transmitting controller 2, where an imaging time $t_B$ of the signal for B-mode and an imaging time $t_{CFM}$ of the signal for CFM are calculated and the sending wave sequence composed of repetition of $t_B$ and $t_{CFM}$ is determined. Following the sending wave sequence, ultrasonic waves are irradiated toward the object from an ultrasonic transducer 1 (hereinafter referred to as transducer 1). The transducer 1 has a structure in which plural piezoelectric devices are arranged one-dimensionally or two-dimensionally. When the transmitting trigger of the signal for B-mode or the signal for CFM comes in from the transmitting controller 2, sending wave signals that are electronically given time delays necessary to converge ultrasonic waves at a predetermined depth are inputted to the devices of the transducer 1 through an A/D converter not illustrated here. The sending wave signal is reflected by a reflector insider the object as an echo signal, which is received by the piezoelectric devices of the transducer 1. The echo signals of ultrasonic waves transmitted as the signal for B-mode are sent to a B-mode image construction unit 3 after reception, and are subjected to addition processing after being subjected to both gain correction according to a focal length and correction of time delays that are generated among the devices according to the focal length, whereby a one-dimensional signal along the depth direction, called a raster signal, is constructed. Plural raster signals obtained by two-dimensionally scanning a converged ultrasonic wave are subjected to envelop detection and interpolation among scanning lines to construct the B-mode image that reflects a reflectivity of the object to the ultrasonic wave. The B-mode image is divided into a multiple motion measurement areas by a motion detector 4, and the motion vector of the object is measured in each motion measurement area. The motion vector is obtained by cross-correlation processing of the motion measurement areas that are set on the same portion on two of the B-mode images. The motion vectors obtained in the respective measurement areas are sent to a time-series CFM signal reconstruction unit 6.

Next, when a signal trigger for CFM is inputted from the transmitting controller 2, the transducer 1 will perform transmitting/receiving of the signal for CFM, and a receiving unit for CFM signal 5 will capture the received signal. Unlike the signal for B-mode, transmitting/receiving of the signal for CFM is performed plural times in each raster. In the time-series CFM signal reconstruction unit 6, the CFM measurement region is set on the first-taken-in signal for CFM in each raster, and the signals for CFM corresponding to the same area as the set-up area is collected based on the measured motion vector from the signals for CFM being captured by the second time or later time to construct the time-series CFM signals. The time-series CFM signals are subjected to autocorrelation processing in an autocorrelation unit 7, and a mean velocity of a blood flow and a dispersion value are calculated. The CFM measurement region in which autocorrelation processing was performed is converted to a two-dimensional image data that is rendered in multiple colors according to the velocity of a blood flow and its direction and the data is sent to a display 8. In the display 8, the two-dimensional image data constructed with the multiple CFM measurement regions is reconfigured into one CFM two-dimensional image that covers the whole object and is displayed on a screen.

Figure 3:
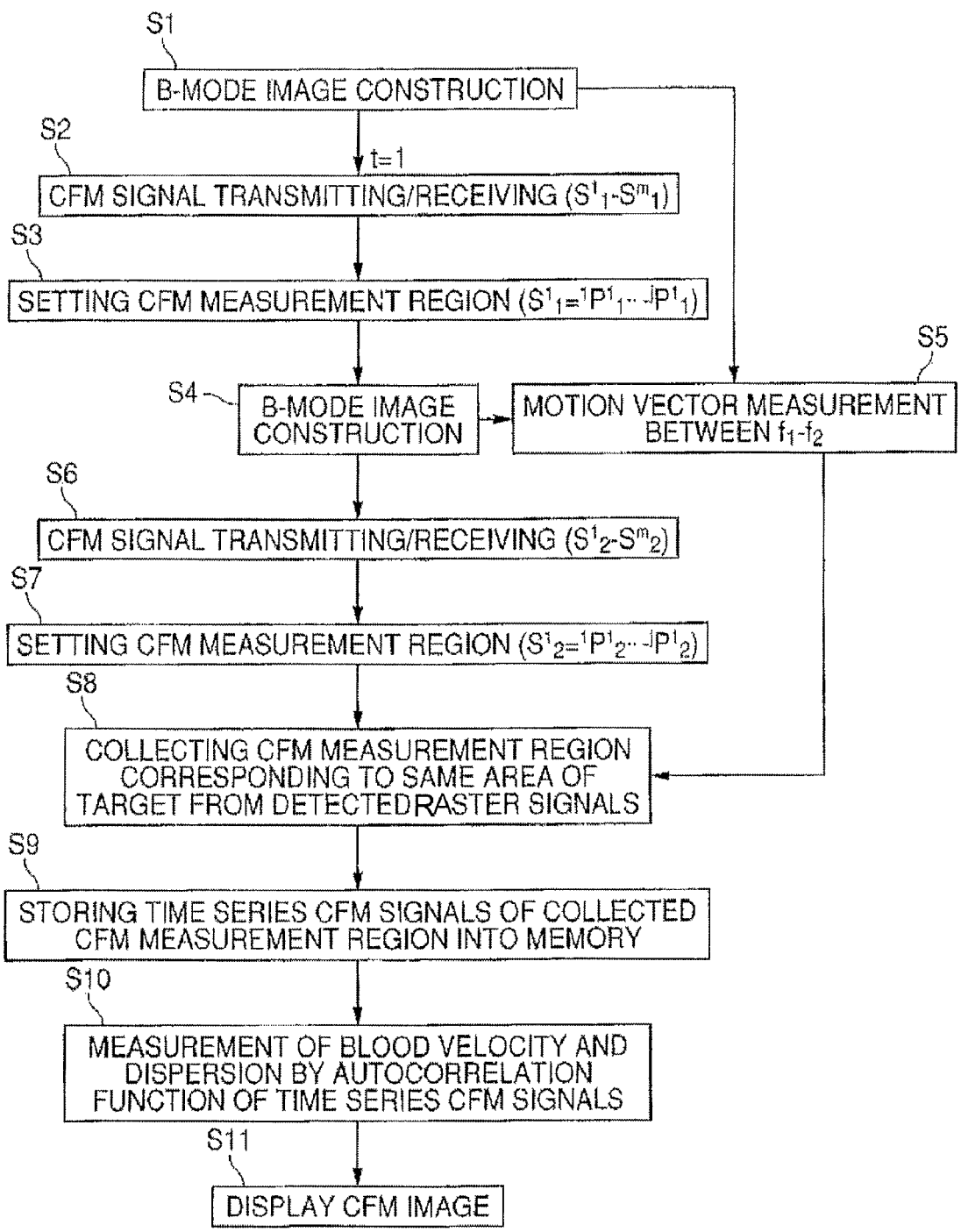
FIG. 3 is a flowchart explaining a signal processing process from wave transmitting/receiving of a signal for B-mode and a signal for CFM in the one type of blood-flow image display equipment of the first embodiment.

Next, a process of from transmitting/receiving of the signal for CFM to construction of the CFM image, through correction processing of the object motion and creation of the time-series CFM signals, will be explained using a flowchart shown in FIG. 3 and the sending wave sequence shown in FIG. 4. FIG. 4A shows timing of B-mode imaging ON and OFF, and FIG. 4B shows timing of CFM imaging ON and OFF. $f_1$ and $f_2$ indicate the B-mode images used for motion vector measurement. S indicates the signal for CFM for each raster and its superscript and subscript denote a raster number (maximum No. m) and the number of transmitting/receiving of a signal in each raster, respectively. P indicates a motion correction block of CFM. A superscript on the left-hand side of P indicates a block number given along the depth direction (sequentially from an area nearest the transducer). A superscript and a subscript on the right-hand side of P indicate, like the signal for CFM S, a raster number (maximum No. m) and the number of transmitting/receiving of a signal in each raster (maximum n), respectively.

First, the B-mode image $f_1$ for measuring the motion vector is constructed (Step 1). Next, the sending wave signal trigger for CFM is inputted to set the transducer in a CFM imaging mode, and in each raster, the first CFM signal in the packet ($S^1_1$–$S^m_1$) is captured (Step 2). The each detected raster signal is divided into j CFM motion correction blocks ($S^1_1$=$^1P^1_1$–$^jP^1_1$) (Step 3). The number j of CFM motion correction blocks being set on each raster is 8 to 12, although it depends on the field of view of the CFM image. Then, the B-mode image $f_2$ is captured (Step 4), and the motion vector produced between $f_1$ and $f_2$ is measured by a least square method or cross-correlation calculation (Step 5). Measurement of the motion vector is performed in each of the plural motion measurement areas being set on the B-mode image. Next, the sending wave signal trigger for CFM is inputted again, the transducer enter the CFM imaging mode, and in each raster, a CFM signal ($S^1_2$–$S^m_2$) that is the second in the packet is captured (Step 6). The each detected raster signal is divided into j CFM motion correction blocks ($S^1_1$=$^1P^1_1$–$^jP^1_1$) (Step 7).

Based on the measurement result of the motion vector, the signal for CFM corresponding to the same portion as the CFM motion correction block being set on the raster is collected from all the detected raster signals (Step 8), and the time-series CFM signals are stored in memory (Step 9). The time-series CFM signals stored in the memory are subjected to autocorrelation processing and the mean flow velocity and the dispersion value are calculated (Step 10). Since calculation of the mean blood flow velocity of a blood flow and the dispersion value using autocorrelation processing is processing being widely used in common ultrasonic diagnostic equipment, detailed explanation will be omitted. By reconstructing all pieces of the two-dimensional image data that is constructed in the CFM measurement region into a video signal, a blood-flow distribution image (CFM image) of the whole object is constructed and is displayed on a screen (Step 11).

Next, a method specifying how to construct the CFM signal of intra-packet motion correction type based on a measurement result of the motion vector will be described.

A concrete construction method will be explained using FIG. 5. To simplify explanation, it is assumed that the number of rasters is three, the number of the CFM measurement regions being set on each raster is seven, and the signal for CFM is obtained by repeating the ultrasonic scanning in the raster direction three times, a construction of the time-series CFM signals regarding the CFM motion correction block $^1P^1_1$ will be explained. The numerals 401a, 401b, and 401c indicate B-mode images ($f_1$, $f_2$, and $f_3$) obtained when the first, second, and third signals for CFM are scanned in the raster direction. The numerals 402a, 402b, and 402c indicate the objects existing in the image 401a, the image 401b, and the image 401c, respectively. That is, it represents that while the signal for CFM is scanned three times, the object moves from the position 402a to the position 402c passing through the position 402b. The raster signal $S^1_1$ is divided into CFM motion correction blocks $^1P^1_1$ to $^7P^1_1$. The following signals are each divided into seven CFM motion correction blocks similarly: $S^2_1$ and $S^3_1$; $S^1_2$, $S^2_2$, and $S^3_2$, that are obtained by the second scanning of the signal for CFM; and $S^1_3$, $S^2_3$, and $S^3_3$, that are obtained by the third scanning thereof.

Now, consider the case where a CFM motion correction block $^1P^1_1$, on 401a is focused and the time-series CFM signals are constructed with 402a and 402c without considering the motion of the object, $^1P^1_2$ and $^1P^1_3$ are collected. At a stage of collecting $^1P^1_3$, since the object has moved to the position 402c practically, the collected time-series CFM signals do not enables a blood flow to be measured correctly.

Therefore, it is necessary to collect the CFM motion correction blocks corresponding to the same portion of the object using the motion vector measured by the motion detector. The numeral 403 indicates the motion vector of the area in which $^1P^1_1$ was set. A CFM motion correction block $^2P^2_2$ corresponding to the same area as $^1P^1_1$ is collected using this motion vector 403 from a group of signals for CFM ($S^1_2$, $S^2_2$, $S^3_2$) scanned by the second time. When the measurement result of the motion vector in the motion measurement area corresponding to the CFM motion correction block $^1P^1_1$ is (x, y), the motion vectors 403, 404 are estimated to be (x/3, y/3). Doing similarly, a CFM measurement region $^3P^3_3$ is collected using the motion vector 404 (x/3, y/3) from the group of signals for CFM ($S^1_3$, $S^2_3$, $S^3_3$) scanned by the third time.

By performing the above processing on all the CFM measurement regions, the time-series CFM signals that are grouped for the same area of the object are stored in the memory. The grouped signals are subjected to autocorrelation processing, and are used to construct the blood flow distribution. Although in this explanation, explanation for the mutually not-overlapped CFM measurement regions was given, actually it is desirable that the CFM measurement regions are overlapped in order to improve accuracy. If the motion correction blocks do not overlap mutually, the correlation calculation tends to yield an error in a location where an autocorrelation window for detecting a blood flow signal covers a boundary of the correlation blocks.

Figure 6:
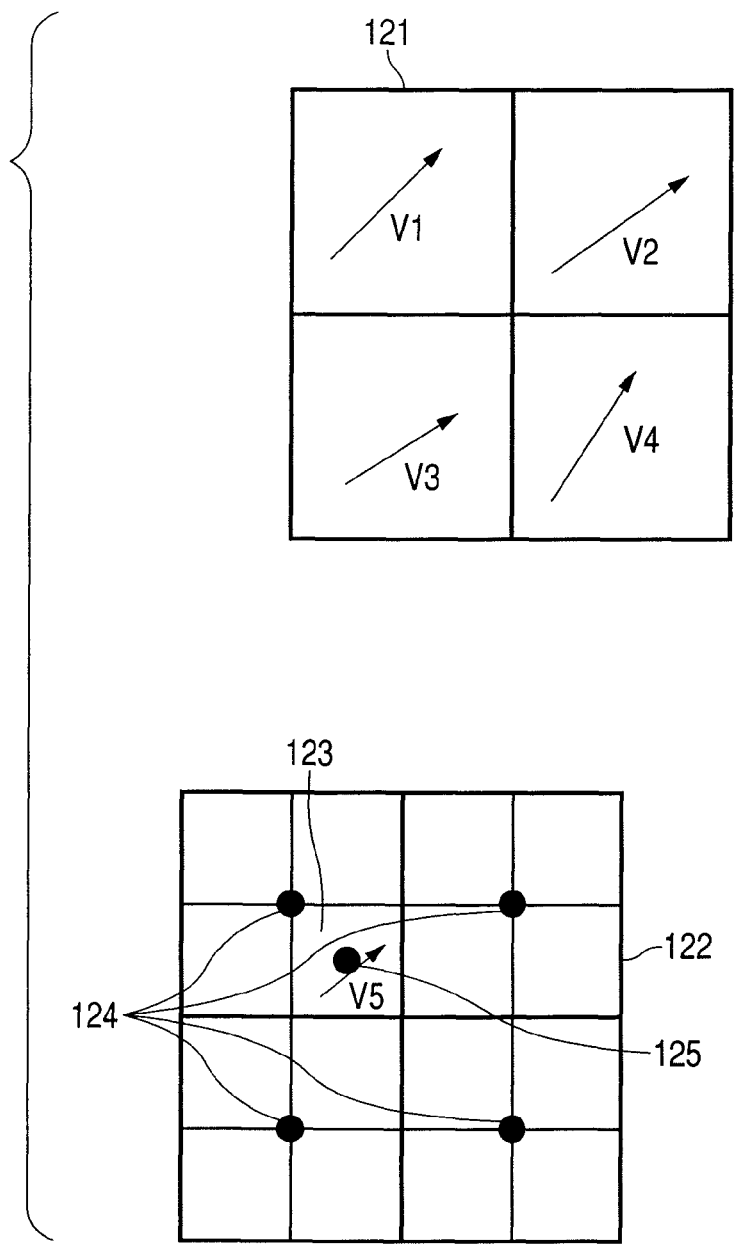
FIG. 6 is a diagram showing a method for estimating a motion vector in a CFM measurement region that is smaller than the motion measurement area in the one type of blood-flow image display equipment of the first embodiment.

If the motion measurement area being set in the B-mode image and the CFM measurement region being set for the signal for CFM are the same, the motion vector in each CFM measurement region is directly measured, Therefore, what the operator should do is to follow the measured motion vector in order to collect an area at the time of constructing the time-series CFM signals. If the motion measurement area is larger than the CFM measurement region, after measuring the motion vector, the motion measurement area is divided again to be of the same size as the CFM measurement region and the motion vector of the divided area is calculated again. The numeral 121 of FIG. 6 shows four motion measurement areas, and the motion vectors in the areas are denoted by V1, V2, V3, and V4, respectively. In order to adjust the size of the motion measurement area to that of the CFM measurement region, each area of the motion measurement areas 121 is divided into four (122) and a motion vector V5 in a divided area 123 is considered. A center of each motion measurement area before division is named 124 and a center of the area 123 after the division is named 125. V5 is obtained by giving a weight that corresponds to a distance from the center of the area 123 to each peripheral area. Now, let ratios of distances to (V1, V2, V3, V4) be ($_x1$, $_x2$, $_x3$, $_x4$) ($_x1 <_x2 =_x3 <_x4$), then V5 is calculated as V5=($_x4 \cdot V1 +_x2 \cdot V2 +_x3 \cdot V3 +_x1 \cdot V4)/(_x1 +_x2 +_x3 +_x4$).

In the body motion correction method described above, the CFM measurement region ($^1P^1_1$) serving as a reference is a first-acquired signal among the group of time-series CFM signals. However, by inverting the motion vector measured by the motion detector 4, it is possible to set a lastly acquired signal for CFM as a reference for body motion correction. By this conversion, the displayed CFM image becomes an image that reflects an actual state of the object more correctly.

Although description was given so far regarding intra-packet motion correction, it is also possible to apply this method to inter-frame motion correction. As shown in FIG. 1, in addition to the inter-packet motion correction that makes a measurement result in the motion detector 4 reflect in the time-series CFM signal reconstruction unit 6, the inter-frame body motion correction is performed in the display 8, whereby it becomes possible to perform frame-accumulation that is not affected by a motion. The inter-frame motion correction can be applied to a method whereby no B-mode imaging is performed in the packet.

Next, a determination process of the sending wave sequence composed of sending wave times ($t_B$, $t_{CFM}$) of the signal for B-mode and the signal for CFM will be explained.

Imaging times ($t_B$, $t_{CFM}$) of the signal for B-mode and the signal for CFM are determined by a targeted blood flow velocity, the motion velocity of the object, and the width of a field of view. Regarding blood measurement, since the signal for CFM is transmitted in the form of a pulse, a measurable velocity of blood flow is limited depending on the repetition period of the pulse. Moreover, regarding motion measurement of the object, there is a limit depending on the size of an ultrasonic beam. A setting procedure of the imaging times ($t_B$, $t_{CFM}$) that considers the above limit will be explained below.

The measurement limit of the blood flow velocity is expressed by $T<1/(2f_d)$, where T denotes a repetition cycle of pulses in each raster and $f_d$ denotes a Doppler frequency produced by the blood flow. Since, the higher the velocity of blood flow, the larger the $f_d$ becomes, the repetition period T of pulses required to measure the $f_d$ becomes smaller, and a measurement range is limited to a shallow portion near the body surface in such velocities. Moreover, in a low-velocity blood flow, a repetition period T becomes large, and accordingly acquisition time of signals required to construct the CFM image becomes long and the frame rate reduces. (However, in the case of T>>2d/c, by acquiring a different raster signal during when waiting lapse of a time T at the same raster position, shortening of the imaging time can be attained.

On the other hand, a measurement limit of the motion vector using the B-mode image depends on the diameter of the transducer, the depth from the transducer to a focusing point, and the size of the received wave beams (Point Spread Function) in the slice direction (a normal direction of an imaging plane) that is determined by a spatial frequency of the sending wave signal. If the size of the motion vector of the slice method is 20% or less of the size of the received wave beam, luminance information necessary for measurement of the motion vector remains in the imaging plane, and measurement of the motion vector within the B-mode image plane by two-dimensional correlation processing is possible. Therefore, denoting the size of a received wave beam by D and the motion velocity of the object by V, a time interval at which the B-mode image is acquired must satisfy $V \cdot t_{CFM} <= 0.2D$ (Condition 1). For example, in the case where the diameter D of the transducer in the slice direction is 4 mm, the focal distance 30 mm, and the ultrasonic wave frequency 10 MHz, the width of the beam in the slice direction becomes approximately 2 mm. The motion velocity of the object is about 1-40 mm/sec, although it depends on the area, a taking-in time of the signal for CFM determined by Condition 1 is set to be in a range of $t_{CFM} < 0.02-0.8$. From Formula 1 and Condition 1, a relation of $n(T+2d/c) \times m <= (0.2D)/V$ (Condition 2) is derived as between the repetition cycle T and the motion velocity V of the object. By combining the imaging times ($t_B$, $t_{CFM}$) that satisfy Formula 1 and Condition 1, the sending wave sequence of the signal for B-mode and the signal for CFM is determined. FIG. 7 shows an outline of the sending wave sequence. According to the signal trigger for B-mode and the signal trigger for CFM being inputted alternately, the B-mode images ($f_1$, $f_2$, - - - ) and the CFM signals ($S_{CFM1}$, $S_{CFM2}$, - - - ) are captured. An acquisition time of a signal for CFM $t_{CFM}$ is set to be as long as possible, and the quantity of the CFM signal being captured during $t_{CFM}$ and a procedure of capturing them in are determined by the blood flow velocity (time T).

A concrete sending wave sequence that corresponds to a concerned velocity region will be explained using FIGS. 8, 9, 10, 11, 12, and 13. In FIG. A of each figure, "high" indicates B-mode imaging ON, and "low" indicates B-mode imaging OFF; in FIG. B, similarly, "high" and "low" indicate imaging time of CFM ON and OFF, respectively. f indicates the B-mode image used for the motion vector measurement. S indicates the signal for CFM of each raster, and a superscript and a subscript indicate a raster number (up to a maximum m) and the number of times in a packet, or (up to a maximum n), respectively.

FIG. 8 shows an example of the sending wave sequence in the case where the motion velocity of the object is fast ($t_{CFM}$ being short) and the blood flow velocity is fast (T being short), in which the B-mode image and the signal for CFM for one raster (n times of transmitting/receiving) are captured alternately and repeatedly, and all the raster signals necessary for construction of the CFM image are received.

Figure 9:
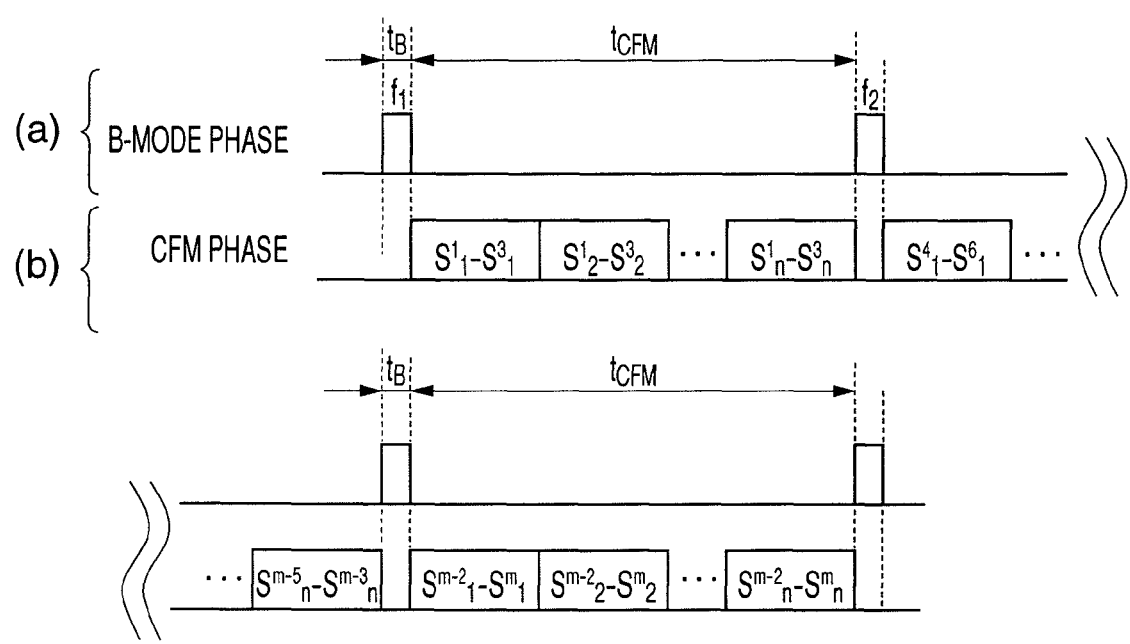
Figure 10:
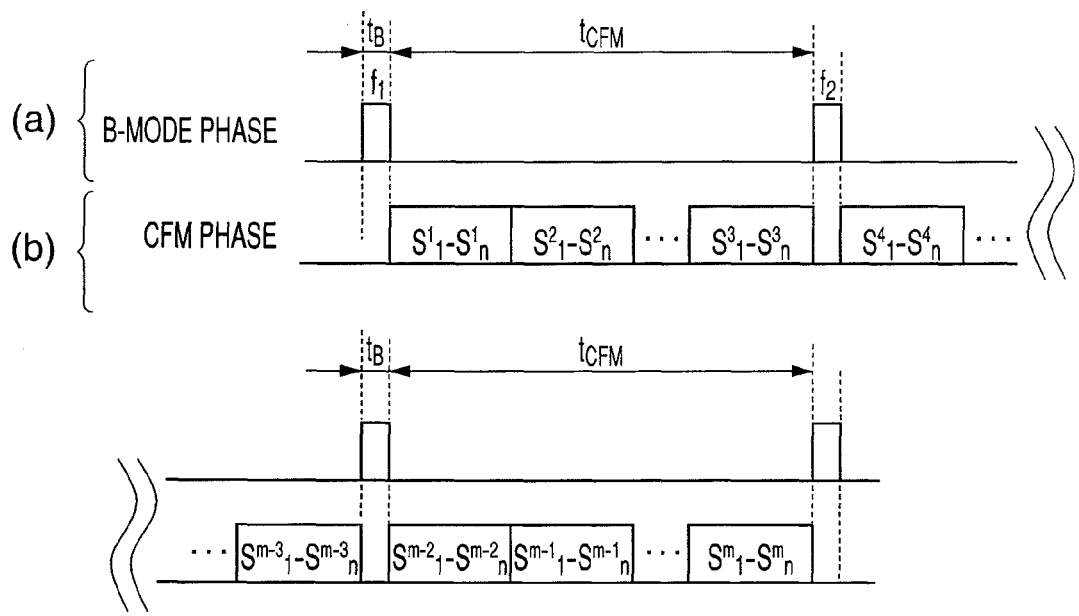

FIG. 9 shows an example of the sending wave sequence that is effective in the case where the motion velocity of the object is comparatively fast ($t_{CFM}$ being short) and the blood flow velocity is slow (T being long), whereby plural rasters are set to be one group and, after receiving the signal for CFM of each raster, the B-mode image is captured. FIG. 9 shows an example where three rasters are grouped into one group. First, the B-mode image is captured, and subsequently ultrasonic scanning of the first raster to the third raster is repeated n times to detect the signals for CFM of the three rasters. In the case where the blood flow velocity is fast and there is no time of detecting a signal of other raster during one packet transmitting/receiving, ultrasonic wave reception may be done for each raster (FIG. 10). The ultrasonic wave transmitting/receiving described above is repeated to detect the signals for CFM of all the rasters.

Figure 11:
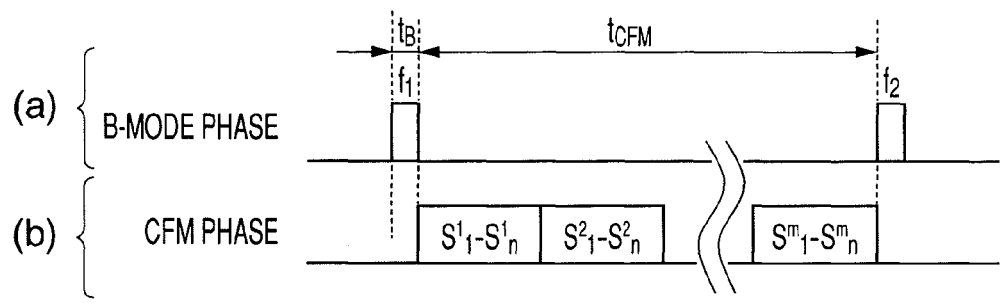

FIG. 11 shows an example of the sending wave sequence in the case where the motion velocity of the object is slow ($t_{CFM}$ being long) and the blood flow velocity is fast (T being short), all the raster signals are continuously transmitted/received without capturing the B-mode image halfway. First, the B-mode image is captured and then the signal for CFM is transmitted/received n times for each raster, which is performed for all the rasters (m).

Figure 12:
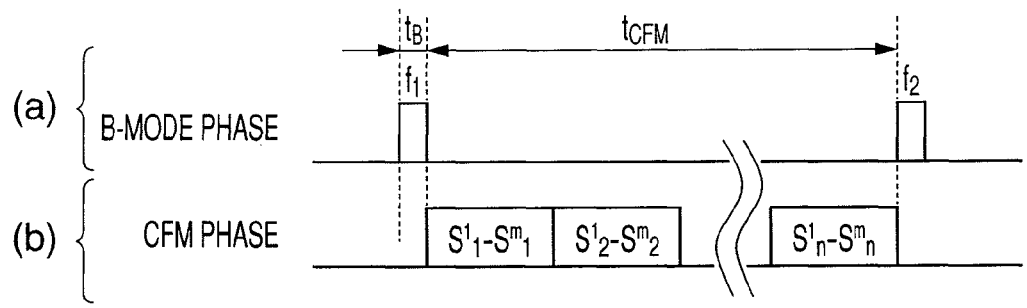
Figure 13:
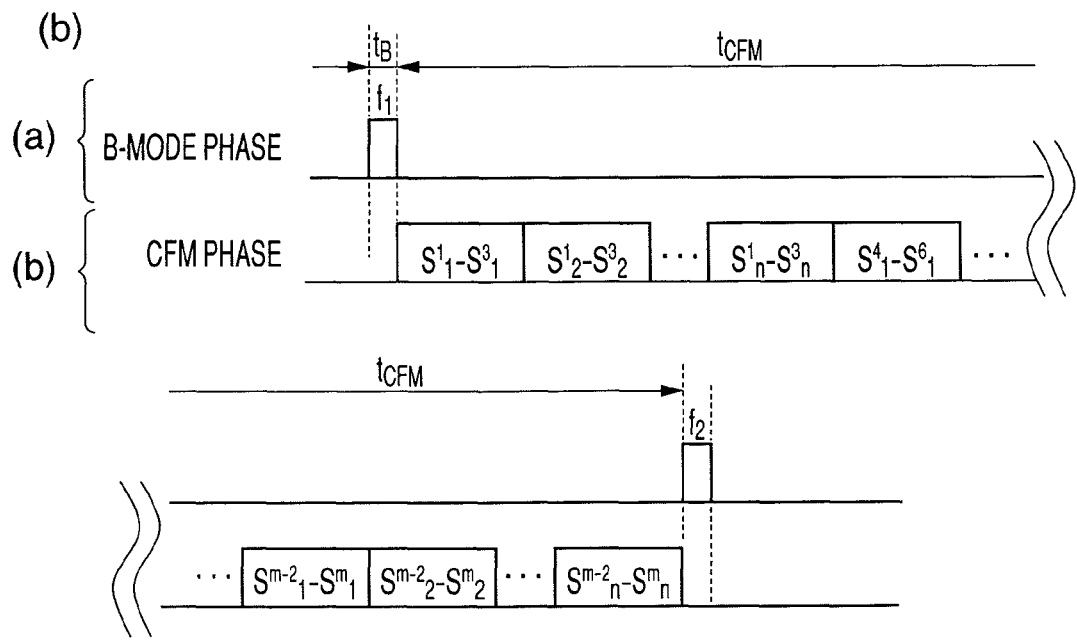

FIG. 12 shows an example of the sending wave sequence in the case where the motion velocity of the object is slow ($t_{CFM}$ being long) and the blood flow velocity is slow (T being long). This is a method whereby first, the B-mode image is captured and subsequently the signal for CFM is transmitted/received by repeating ultrasonic scanning in the raster direction n times.

In the case where the motion velocity of the object is slow ($t_{CFM}$ being long), but a sufficient time to allow ultrasonic scanning of all the rasters (m) cannot be secured, there is conceivable a method for acquiring all the raster signals (FIG. 13) that uses a transmitting/receiving method for forming a raster group in which plural rasters are grouped (not more than m) and ultrasonic scanning in the raster direction is repeated n times in each raster group.

In the case where the motion velocity of the object is slow and $t_{CFM}$ is large enough to allow the signal for CFM to be detected in all the rasters, it is recommended that the B-mode image be captured appropriately during when the signals for CFM are being detected. The reason of this is that, the more the B-mode images are with respect to the amount of signals for CFM used to correct the motion of the object, the much the correction accuracy of motion is improved.

In any of the sending wave sequences shown in FIGS. 8, 9, 10, 11, 12 and 13, it is preferable that a time $t_B$ required to acquire the B-mode image is as short as possible. As means for shortening $t_B$, there is conceivable a method for reducing the number of rasters of the B-mode image to match with the number of rasters of the signal for CFM.

Figure 14:
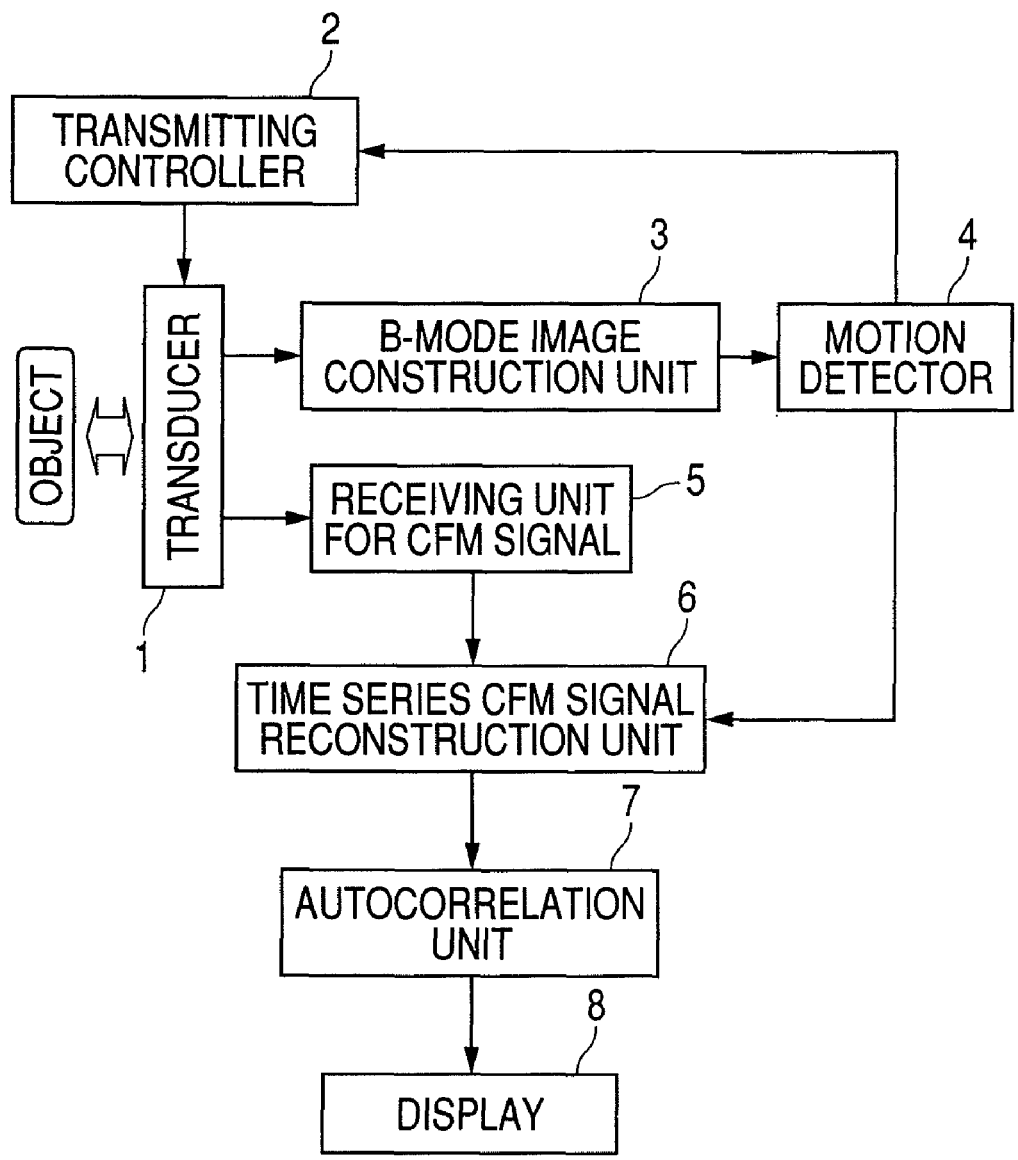
FIG. 14 is a block diagram showing a construction according to a second embodiment of the one type of blood-flow image display equipment of this invention.

The blood-flow image display equipment that follows the block diagram shown in FIG. 1 is a system in which the motion velocity of the object and the blood flow velocity are determined by the operator selecting the object displayed on a screen, and the sending wave sequence of the signal for B-mode and the signal for CFM is determined based on them. The blood-flow image display equipment that follows the block diagram shown in FIG. 14 captures two or more B-mode images and a signal for blood flow measurement as in the first part of the sending wave sequence and measures the body motion of the object and the blood flow velocity. This is a system that determines the sending wave sequence of the signal for B-mode and the signal for CFM based on this measurement result. In the case of this system, since the motion velocity of the object measured by the motion detector 4 is sent to the transmitting controller 2, even when the motion velocity varies during when the operator does operations, the blood flow image can be displayed automatically by an optimal sending wave sequence.

In the blood-flow image display equipment explained above, description was given about the CFM image. However, even in the case of using a power Doppler image, the power Doppler image from which an effect of a body motion is removed can be displayed using similar equipment and flowchart of signal processing except for autocorrelation processing. In power Doppler, instead of autocorrelation processing, the intensity of a Doppler frequency is calculated using the obtained signal for CFM. Although information in a blood flow direction is not acquired, a blood vessel can be imaged with high sensitivity as compared with the CFM image, since the intensity of all the signals whose frequencies are shifted by the blood flow are imaged.

Second Embodiment

Figure 15:
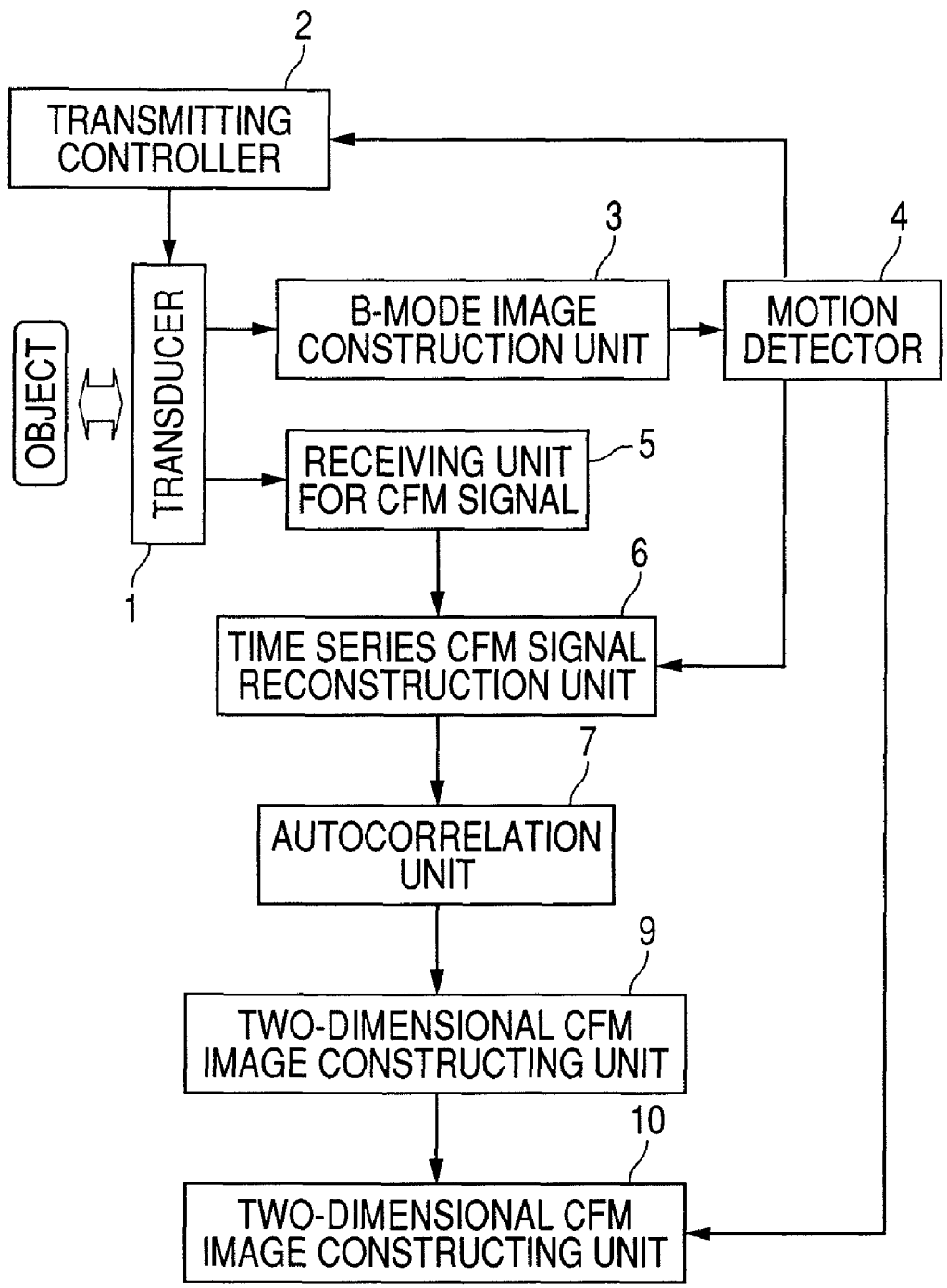
FIG. 15 is a block diagram showing a construction of one type of three-dimensional blood-flow image display equipment of the second embodiment.

Hereafter, three-dimensional blood-flow image display equipment using the blood-flow image display equipment of the first embodiment will be described using the block diagram of FIG. 15.

Several structures of a transducer used to capture three-dimensional information of an object and several imaging methods are conceivable. In the case where the transducer 1 is a one-dimensional array, in order to capture three-dimensional information, it is necessary to make the transducer scan in the slice direction mechanically. To implement the scanning method, the operator may scan the transducer 1 manually or the transducer 1 may be scanned automatically by motor control. In the case where the transducer 1 is of a two-dimensional array, since an arbitrary imaging plane can be captured without mechanically moving the transducer, it is possible to easily capture three-dimensional information of the object by scanning the imaging plane in the slice direction automatically.

Figure 16:
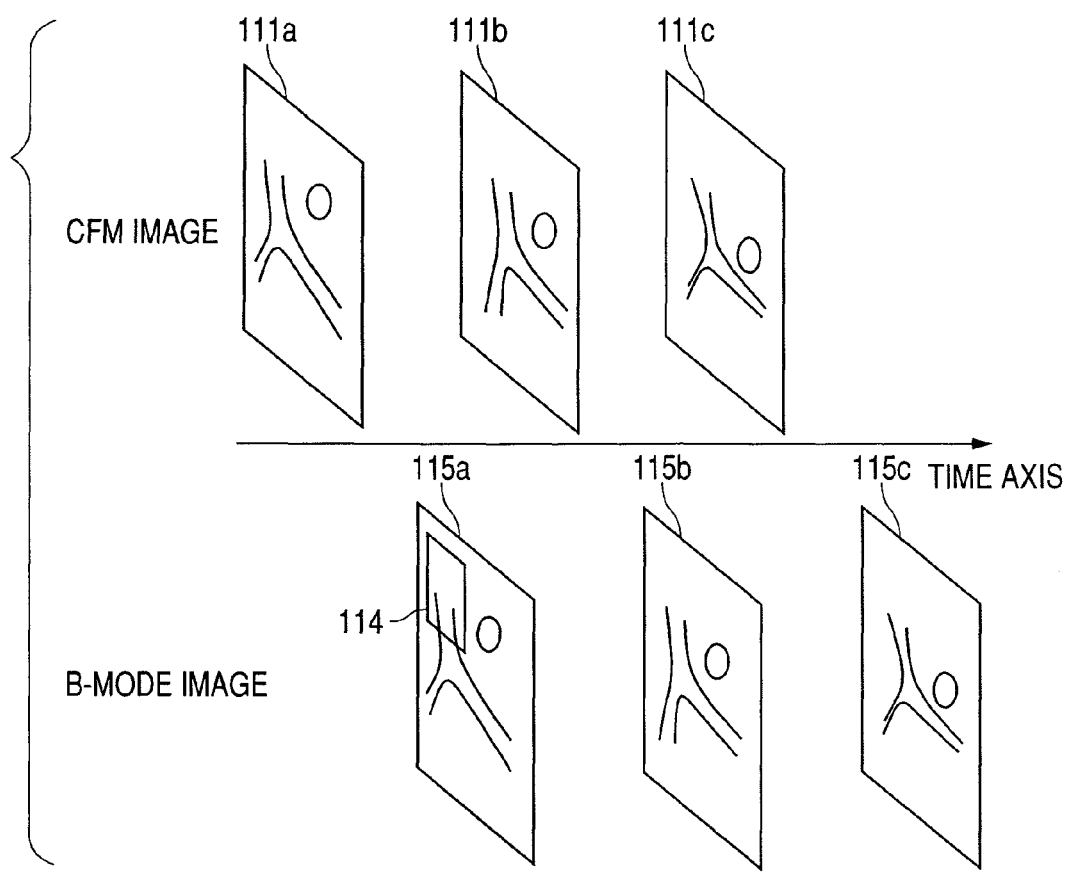
FIG. 16 is a diagram showing a two-dimensional CFM image for constructing a three-dimensional image and a B-mode image used for body motion correction in the one type of three-dimensional blood-flow image display equipment of the second embodiment.

A construction of the equipment responsible for transmitting/receiving of ultrasonic waves by the transducer 1 to construction of the two-dimensional CFM image from which the motion of the object is removed and a process of signal processing are the same as those in the first embodiment. The signals subjected to autocorrelation processing are used to construct the two-dimensional CFM image from which an effect of the motion of the object is removed in the two-dimensional CFM image constructing unit 9 and are retained in the memory. The numeral 111 of FIG. 16 shows the two-dimensional CFM image being retained. Next, ultrasonic wave transmitting/receiving for acquiring the two-dimensional CFM images that are slightly shifted from one another in the slice direction are performed following the sending wave sequence from the transmitting controller 2, and a new two-dimensional CFM image is retained in the memory in the two-dimensional CFM image constructing unit 9 (the numeral 111b of FIG. 16). Next, the two two-dimensional CFM images 111a, 111b are sent to a three-dimensional CFM image constructing unit 10, and are used to construct a three-dimensional CFM image in which the motion of the object is corrected.

Next, a correction method of the motion of the object will be explained using FIG. 16. The sending wave sequence of ultrasonic signals for constructing the two-dimensional CFM image was described in the first embodiment. In that sequence, in order to remove the effect of the motion of the object from the signal for CFM, the B-mode image is acquired without fail before the start of transmitting of the signal for CFM and after the receiving of a last signal for CFM for constructing the two-dimensional CFM image. Therefore, in the second embodiment, a B-mode image 115a immediately after the acquisition of the two-dimensional CFM image 111a and a B-mode image 115b immediately after the acquisition of the two-dimensional image 111b are retained in the motion detector 4, and a motion produced between the CFM image 111a and the CFM image 111b are corrected by the two of the B-mode images 115a, 115b. Since the each acquired two-dimensional CFM image is an image in which a motion is corrected, motion correction between the CFM image 111a and the CFM image 111b is performed using a reference area 114 being set on the B-mode image 115a, motion correction over the whole two-dimensional image is performed automatically. A method for correcting a body motion is the same as the method that was preformed in constructing the two-dimensional CFM image. An area that is most consistent with the reference area 114 is searched from the B-mode image 115b by cross-correlation calculation or a least square method. The two-dimensional CFM images 111a and 111b are reconstructed so that the area obtained by the search and the reference area are overlapped, whereby the three-dimensional CFM image from which the effect of the motion of the object has been removed is constructed.

The motion correction regarding a two-dimensional CFM image 111c that is newly captured is performed similarly. The B-mode image that is captured after the two-dimensional CFM images 111b, 111c are acquired is used to correct a motion at the time of constructing a three-dimensional CFM image based on a reference area that is newly set on the B-mode image (115b and 115c). Performing motion correction and image reconstruction on the two-dimensional CFM image of the whole object constructs the three-dimensional CFM image from which the effect of the motion is removed.

Third Embodiment

Figure 17A:
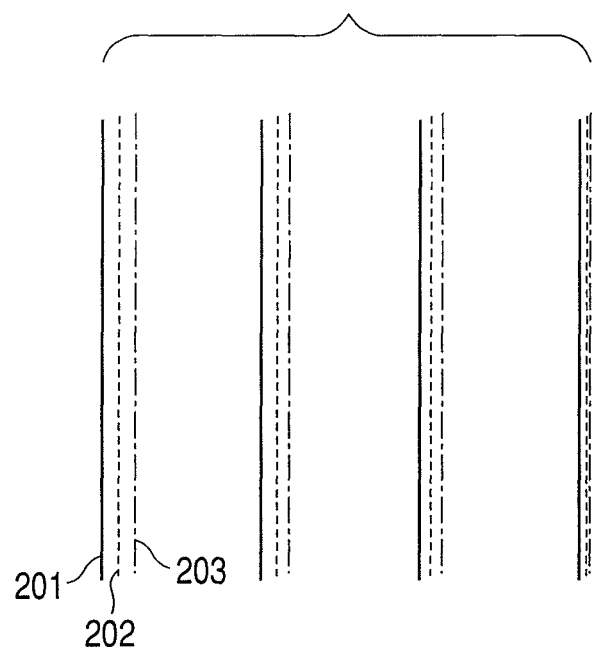
Figure 18:
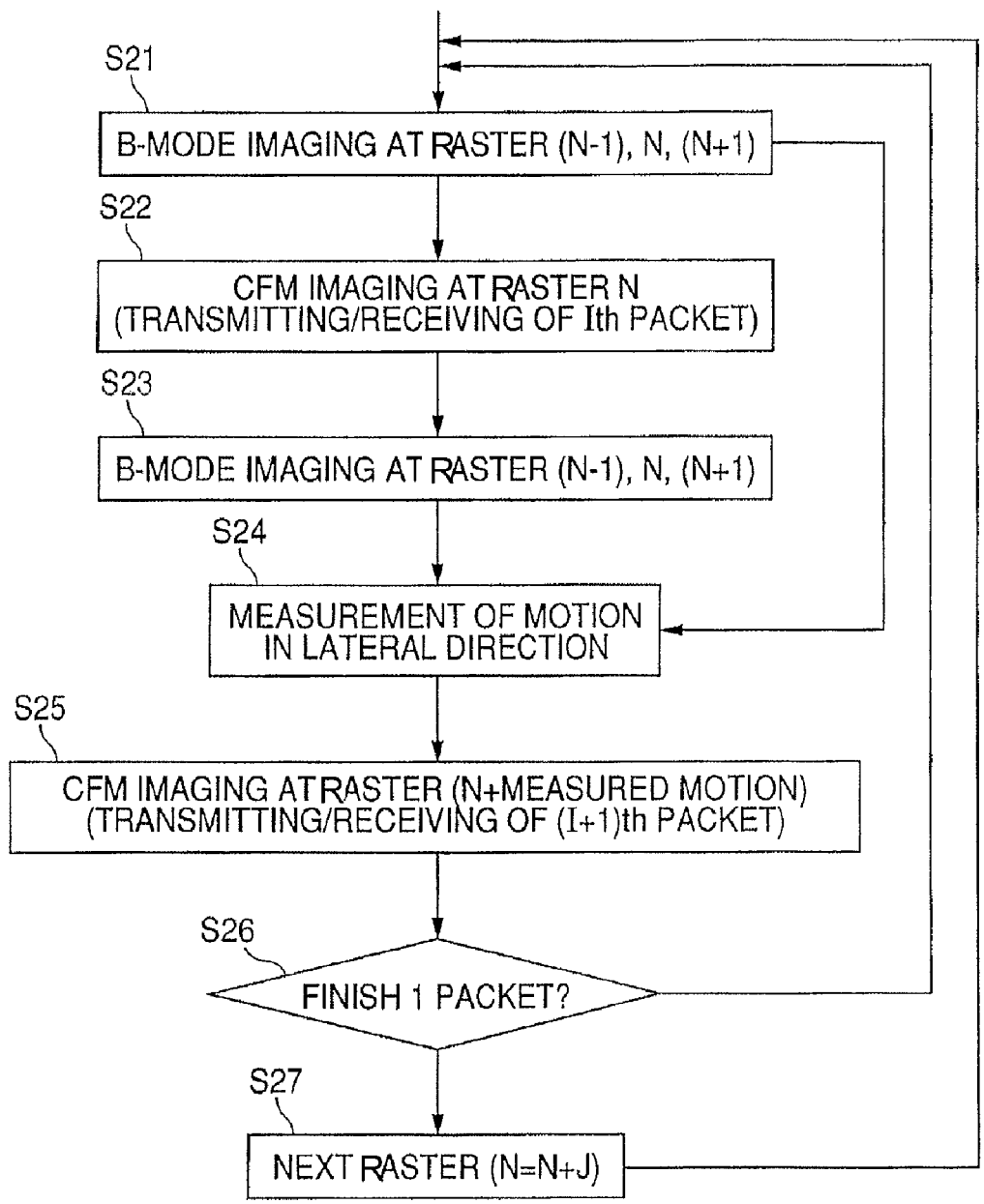
FIG. 18 is a flowchart explaining a signal processing process of B-mode imaging and CFM imaging in the one type of blood-flow image display equipment of the third embodiment.

In the first embodiment, the result of motion estimation in the B-mode imaging is used to collect data that corresponds to the same area from pieces of CFM data having already been acquired. In this third embodiment, a raster position at which the next transmitting/receiving is done is corrected by using a result of motion estimation in the B-mode imaging, and accordingly a smaller motion is corrected. That is, by performing tracking to the motion, not by specifying a raster position to space, a raster that is associated with each tissue in an object organ is defined. This embodiment is effective especially in order to image a low-velocity blood flow in a peripheral blood vessel where the body motion and the velocity of the blood flow are of the same order. Since conventionally, a difference between the velocities was used to remove the body motion, imaging of a low-velocity blood flow was difficult. In this embodiment, motion estimation by B-mode imaging is performed between transmitting/receiving in a packet, and an estimation result is reflected to a position of the next raster of transmitting/receiving for CFM, as shown in FIG. 17A. In this figure, a solid line 201 represents a raster in the first transmitting/receiving in the packet, a dashed line 202 represents a raster of the second transmitting/receiving in the packet, and an alternate long and short dash line 203 represents a raster of the third transmitting/receiving in the packet. An imaging sequence is as follows: as shown in FIG. 18, the B-mode imaging is performed on totally three rasters, that is, a raster to which attention is paid (in FIG. 18, it is assumed to be N-th raster) and two rasters adjacent to it by ±1 (Step 21), the CFM imaging is performed at the N-th raster (Step 22), the B-mode imaging is done again using three rasters of N and N±1 (Step 23), the amount of a motion in the lateral direction is estimated (Step 24), second transmitting/receiving for CFM is performed based on this estimation result (Step 25). This operation is repeated for one packet. After this is completed, the focused raster for CFM is moved and the index N is changed to N+J. Since a raster interval of the CFM is usually coarser than a raster interval of the B-mode, J satisfies J>1. By repeating this operation, imaging of one screen is completed.

Figure 17B:
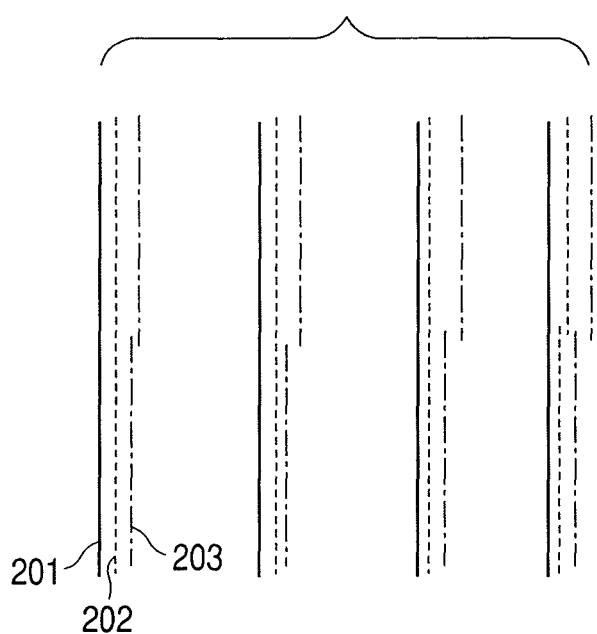

If, in the B-mode imaging, motion correction accuracy has been improved by increasing the number of rasters by means of inter-raster interpolation of received double beams and the RF data without increasing an imaging time, it will be effective to perform tracking of a raster position. In linear scanning and convex scanning of the conventional analog ultrasonic diagnostic equipment, since an interval of rasters must be constant and a delay time pattern of each device for beam forming of transmitting/receiving must be invariant to a diameter motion, there is the case where tracking of a raster position is unrealistic. However, the digital ultrasonic equipment of recent years can apply a different delay time for each raster, which enables this method to be applied to such a motion that makes the raster interval uneven, such as of a tissue deforming attended with distortion. Especially when extraction of a low-velocity blood flow is a main concern, the signal is detected for several stages divided in the depth direction, as shown in FIG. 17B, and the tracking of the raster position is done for each depth separately. This procedure enables a motion being not uniform in the depth direction to be tracked with high accuracy.

Conventionally, the diagnostic equipment follows a moving object by shortening an imaging time. Following the object, while correcting its position, enables visualization suited to estimation of a low-velocity blood flow even when the object moves at a low velocity.

The motion estimation method can be realized by performing the method described in the first embodiment. However, in order to make a circuit scale small, there is also a method whereby only the amount of motion in the lateral direction is estimated in tracking the raster to be reflected in beam forming, and in the later half of the processing, only motion correction in the depth direction is performed. As methods of estimating a motion only in the lateral direction, there are methods as follows: a method whereby, for example, pieces of B-mode image data are summed in the depth direction to obtain one-dimensional data that is compressed in the depth direction and this data is subjected to one-dimensional correlation operation; and a method of acquiring a signal that uses an aperture weight having sensitivity for a motion in the lateral direction, called vector Doppler. In the case where the motion cannot be assumed completely uniform in the depth direction, having two or more ways of this processing is also effective for increase of accuracy. If a part that is specialized in tracking processing of a raster is separated from a circuit and thus a scale of the circuit can be made small, it will be extremely advantageous in installing the circuit in the equipment because a freedom of selecting an ASIC to be installed is increased.

What is claimed is:

1. A blood-flow image display equipment, comprising:
   an object, and second the rough value of blood flow velocity information about the object to a transmitting controller that determines and controls the transmission of a sending wave sequence;
   an ultrasonic transducer that transmits and receives ultrasonic waves according to the sending wave sequence;
   an ultrasonic two-dimensional image construction unit that constructs ultrasonic two-dimensional images using received ultrasonic waves;
   a vector measurement unit that measures a motion velocity of the object using a motion vector obtained from the ultrasonic two-dimensional images;
   a blood flow signal receiving unit that receives signals related to blood flow, and sets a blood-flow measurement area;
   a signal construction unit that constructs a time-series blood flow image, and that based on the motion vector measured by the vector measurement unit collects and retains signals related to blood-flow from the blood flow measurement area;
   an autocorrelation calculation unit that performs autocorrelation processing on the signals related to blood flow that are retained for use in constructing a time-series blood flow image, and measures a blood flow velocity and a dispersion value of that blood flow measurement area; and
   a blood flow image display unit that constructs and displays the time-series blood flow image that is rendered in multiple colors according to the measured blood flow velocity and a blood flow direction;
   wherein the sending wave sequence includes a signal for creating the ultrasonic two-dimensional images, and a signal for creating the time-series blood flow image; and
   wherein the transmitting controller further changes the sending wave sequence depending on the measured motion velocity of the object and the measured blood flow velocity.

2. The blood-flow image display equipment according to claim 1,
   wherein measurement of the motion vector is done two-dimensionally using two or more ultrasonic two-dimensional images, and the signals related to blood flow from the blood-flow measurement area are collected both in a depth direction and in a raster direction based on a measurement result of the motion vector.

3. The blood-flow image display equipment according to claim 1,
   wherein an acquisition time for the signals related to blood flow is determined by the motion velocity of the object.

4. The blood-flow image display equipment according to claim 1,
   wherein, when the motion velocity of the object varies, the sending wave sequence is changed based on the measurement result of the motion vector.

5. Image display equipment that uses the blood flow image display equipment according to claim 1, further comprising:
   a two-dimensional blood-flow image construction unit that retains a plurality of two-dimensional blood flow images different from one another in a slice direction normal to the two-dimensional blood-flow image, and from which effects of motions are removed, respectively; and
   a three-dimensional blood-flow image construction unit that constructs a three-dimensional blood flow image by motion correction processing and image reconstruction processing based on a measurement result of the motion vector by ultrasonic two-dimensional images using the two-dimensional blood flow images;
   wherein the three-dimensional blood flow image is reconstructed based on the results of measuring the motion vector by using the ultrasonic two-dimensional images.

6. The three-dimensional blood-flow image display equipment according to claim 5,
   wherein measurement of the motion vector produced among a plurality of two-dimensional blood flow images is performed using a reference area on the ultrasonic two-dimensional images acquired in constructing two-dimensional blood flow images;
   wherein the reference area on the ultrasonic two-dimensional image, with an area almost the same in size as the blood-flow measurement area, is set up in order to perform autocorrelation calculation on the two-dimensional blood flow image.

7. The blood-flow image display equipment according to claim 1,
   wherein a raster position is moved based on a measurement result of the motion vector.

8. Image diagnostic equipment, comprising:
   a measurement area setting unit that sets a first and second measurement areas of an object;
   a transducer that transmits and receives ultrasonic signals in the first and second measurement areas, the transmitted ultrasonic signals being sequenced so as to enable creation of both a blood flow image and an ultrasonic two-dimensional image of the object;
   a body motion measurement unit that detects and measures a motion velocity of the object in the first and second measurement areas;
   a signal collection unit that collects and compares an ultrasonic signal received from the first measurement area and an ultrasonic signal received from the second measurement area, and collects a group of temporal signals about the first and second measurement areas;
   a signal processing unit that detects shifts among any of the ultrasonic signals in any of the first measurement area an second measurement area, and detects a motion velocity of either the first measurement area or the second measurement area, and directly or indirectly instructs the transducer to change the sequence of transmitted ultrasonic signals in response to a detected shift or a detected velocity; and a display unit that displays a blood flow image or an ultrasonic two-dimensional image of the object constructed based on detection results of the signal processing unit.

9. The image diagnostic equipment according to claim 8,
wherein the signal collection unit collects a group of temporal signals about the same areas of the blood vessel including the object.

10. The image diagnostic equipment according to claim 8, wherein ultrasonic signals received from the first measurement area and ultrasonic signals received from the second measurement area constitute respective groups; and wherein each group further includes a plurality of temporal signals.

* * * * *